United States Patent [19]

Gaffar et al.

[11] Patent Number: 5,135,738
[45] Date of Patent: Aug. 4, 1992

[54] ARTICLE COMPRISING A DISPENSING CONTAINER OF POLYMERIC MATERIAL IN CONTACT WITH AN ANTIPLAQUE ORAL COMPOSITION WITH WHICH IT IS COMPATIBLE

[75] Inventors: Abdul Gaffar, Princeton; Richard S. Robinson, Piscataway; Jeffrey Miller, Sayreville; Chimpiramma Potini, E. Brunswick; Michael A. Collins, Keyport; Theresa G. Shackil, Vincetown, all of N.J.

[73] Assignee: Colgate-Palmolive Company, Piscataway, N.J.

[21] Appl. No.: 427,660

[22] Filed: Oct. 26, 1989

Related U.S. Application Data

[63] Continuation-in-part of Ser. No. 398,566, Sep. 25, 1989, Pat. No. 5,032,386, and a continuation-in-part of Ser. No. 398,592, Aug. 25, 1989, and a continuation-in-part of Ser. No. 398,605, Aug. 25, 1989, abandoned, and a continuation-in-part of Ser. No. 398,606, Aug. 25, 1989, abandoned, and a continuation-in-part of Ser. No. 399,669, Aug. 25, 1989, abandoned, and a continuation-in-part of Ser. No. 410,682, Sep. 21, 1989, abandoned, each is a continuation-in-part of Ser. No. 291,712, Dec. 29, 1988, Pat. No. 4,894,220.

[51] Int. Cl.$^5$ .................................................. A61K 7/16
[52] U.S. Cl. ........................................... 424/49; 424/52; 424/57; 424/58; 206/277; 206/524.1; 206/524.3; 222/107; 514/718; 514/721; 514/900; 514/901; 514/902
[58] Field of Search .................. 424/49, 50, 52, 57

[56] References Cited

U.S. PATENT DOCUMENTS

| 3,956,480 | 5/1976 | Dichter et al. | 424/54 |
| 4,022,880 | 5/1977 | Vinson et al. | 424/50 |
| 4,510,127 | 4/1985 | Chang | 424/52 |
| 4,595,613 | 6/1986 | Tavss et al. | 222/92 |
| 4,716,034 | 12/1987 | Schelm | 424/49 |
| 4,830,221 | 5/1989 | Mazzanobile | 424/49 |

Primary Examiner—Thurman K. Page
Assistant Examiner—James M. Spear
Attorney, Agent, or Firm—Robert L. Stone; Murray M. Grill; R. C. Sullivan

[57] ABSTRACT

An oral composition, such as a paste or gel dentifrice or a liquid mouthwash, containing a substantially water insoluble non-cationic antibacterial agent, such as triclosan, which, when used to clean the teeth or rinse the mouth, acts to decrease plaque on the teeth, is packaged in a dispensing container or bottle which includes a solid polymeric material, such as polyfluoroethylene, which is compatible with the antibacterial agent so that excessive loss of anti-plaque acitivity of such agent on storage is avoided. Alternatively, various other polymers may be employed as container parts, which normally would cause excessive losses of anti-plaque action of the antibacterial agent in the composition but such action is countered by the presence of a stabilizer, such as a terpene, e.g., limonene, in the oral composition formula. Also described is a method for inhibiting development of plaque on teeth.

24 Claims, 2 Drawing Sheets

ARTICLE COMPRISING A DISPENSING CONTAINER OF POLYMERIC MATERIAL IN CONTACT WITH AN ANTIPLAQUE ORAL COMPOSITION WITH WHICH IT IS COMPATIBLE

This application is a continuation-in-part of each of U.S. patent application Ser. Nos. 07/398,566, now U.S. Pat. No. 5,032,386, 07/398,592, 07/398,605, abandoned, 07/398,606, abandoned, and 07/399,669, abandoned, all of which were filed on Aug. 25, 1989, and of Ser. No. 410,682, abandoned, filed Sep. 21, 1989 and all of which are continuation-in-part of Ser. No. 07/291,712 now U.S. Pat. No. 4,894,220 filed Dec. 29, 1988.

This invention relates to package anti-plaque oral compositions which comprise an anti-plaque antibacterial agent such as 2', 4, 4'-trichloro-2-hydroxy-diphenyl ether (THDE), as an effective anti-plaque component, which compositions are package in a container which includes a polymeric plastic material in contact with the oral composition, which plastic is compatible with the antibacterial agent in the composition. Although various plastics may diminish the anti-plaque action of the mentioned antibacterial agents, certain plastics, such as polyfluoroethylene and polyvinyl chloride, have been found to be compatible with THDE and it has been discovered that they do not cause excessive losses of antibacterial and anti-plaque activities of contained oral compositions on storage, at room or elevated temperatures. Even when the contacting plastic part(s) of the container is/are of a plastic which is not in itself entirely compatible with the antibacterial compound, compatibility can be improved by incorporating in the oral composition a stabilizing proportion of a stabilizer for the antibacterial compound, such as a terpene, e.g., limonene, or an essential oil (natural or synthetic), which may be present in a flavoring material for the oral compositions. Such stabilizing material is present in sufficient proportion so that the oral composition, as packaged and dispensed, is an effective anti-plaque composition, the production of which is an object of this invention. Included within the invention is a method of contacting oral surfaces with oral compositions containing effective proportions of anti-plaque agent. Also within the invention is a toothbrush having on its bristles an effective proportion of an anti-plaque dentifrice.

Plaque on teeth is considered to be causative factors of negative periodontal conditions, and dental plaque is a precursor of calculi. Plaque may form on any part of the tooth surface, including the gingival margin. It makes the teeth appear dull and in addition to promoting development of calculi, it has been implicated in occurrences of gingivitis. Therefore, oral compositions that contain anti-plaque components which prevent or inhibit the development of plaque on the teeth are valuable dental care aids.

Although it has been known that antimicrobial agents in oral compositions may reduce plaque, sometimes being especially effective in combinations with other materials, various such antibacterial compounds possess disadvantageous properties which mitigate against their employment in such oral compositions. For example, cationic antibacterial compounds, such as quaternary ammonium halides, tend to discolor the teeth and may be inactivated by the presence of anionic materials in the oral preparations (and often it will be desirable to employ anionic surfactants or detergents in oral compositions).

Essentially water insoluble halogenated (and often hydroxylated) diphenyl ethers, such as THDE (triclosan) and 2,2'-dihydroxy-5,5'-dibromo-diphenyl ether (DDDE), are effective anti-plaque antibacterial agents but can be inactivated by nonionic surfactants and by many plastics, as has been discovered by applicants. Thus, an object of this invention has been to incorporate antibacterial anti-plaque agents, such as halogenated diphenyl ethers, particularly THDE and DDDE, and similar anti-plaque agents in oral compositions, and to store such compositions in and dispense them from packages or containers in which they will not lose an excessive proportion of the activity of such antibacterial agent on storage, before intended use. In prior art triclosan dentifrices, as delivered from the dispenser, the triclosan delivery has not been in an effective amount to significantly reduce plaque when employed once or twice daily at 1.5 g./use with one minute brushings, which is considered to approximate normal brushing practice. To be effective, such uses should result in at least 25% reduction in plaque after three weeks' use, compared to three weeks' use of a control toothpaste in the same manner.

The most preferred antibacterial anti-plaque component of the present packaged oral compositions is THDE, which is also known as triclosan. Such is disclosed in U.S. Pat. No. 4,022,880 as an antibacterial agent, in combination with an anticalculus agent (which provides zinc ions), and in German patent specification (OLS) No. 35 32 860 in combination with a copper compound. It is also disclosed in European patent application Nos. 0 161 898 and 0 161 899, and in European patent application 0 220 890 it is disclosed in dentifrices with polyethylene glycol and oil based flavor.

Various oral compositions or dental preparations are known, including paste, gel, powder, liquid, tablet, lozenge, sachet and packeted dentifrices, liquid and tableted mouthwashes; and professionally applied tooth treating agents (such as tooth hardening compositions, e.g., fluoride solutions). Such products have been packed in deformable tubes, pump dispensers, pressurized dispensers, packets, bottles, jars and other containers. Although deformable or collapsible tubes were initially made of metals, such as lead and aluminum, and bottles were made of glass, in recent years such containers have often been made of synthetic organic polymeric plastics or made of laminates which included such plastics. Interactions between oral compositions and the materials of containers in which they were packed have been known, such as reactions between toothpastes and aluminum containers, and to prevent such reactions containers have been specially treated or different container materials have been employed. However, applicants do not believe that before their invention it had been known to the prior art that some plastic packaging materials could adversely affect the antiplaque activities of halogenated diphenyl ether antibacterial compounds that had been incorporated in oral compositions and packed in containers in which they came into contact with such plastics, nor do they believe that it had been discovered that certain plastics could be employed for such container parts without causing losses of the antiplaque activities of halogenated diphenyl ethers or that losses of such activities of oral compositions packed in contact with "reactive" plastics (which react with, absorb or otherwise reduce the antiplaque activity of the oral composition) could be inhibited or prevented by incorporating in the compositions terpenes, such as limonene, and other components of flavors for oral preparations.

In accordance with certain of its aspects the present invention relates to an oral composition containing an effective anti-plaque proportion of a substantially water insoluble non-cationic antibacterial agent when dispensed, is packaged in a dispensing container which includes a solid polymeric material, such as a synthetic organic polymeric plastic material, in contact with the oral composition, which solid polymeric material is compatible with the antibacterial agent in the presence of the oral composition and does not cause excessive loss of antibacterial and anti-plaque activities of the oral composition on storage in the container (such as at temperatures in the range of 20° to 40° C. for several weeks, preferably up to a year or more). The packaged oral composition is usually a toothpaste, gel dentifrice or mouthwash contained in a deformable dispensing tube, pump dispenser or bottle, respectively, having no plastic parts which adversely affect the antiplaque action of the antibacterial agent, (which is preferably a halogenated diphenyl ether, such as triclosan), or containing in the oral composition a component which inhibits or prevents any such detrimental "reaction" between the antibacterial agent and any plastic part of the container which could otherwise adversely affect the composition's antiplaque action.

The invention will be readily understood from the description thereof in this specification, taken in conjunction with the drawing, in which.

Figure 1:
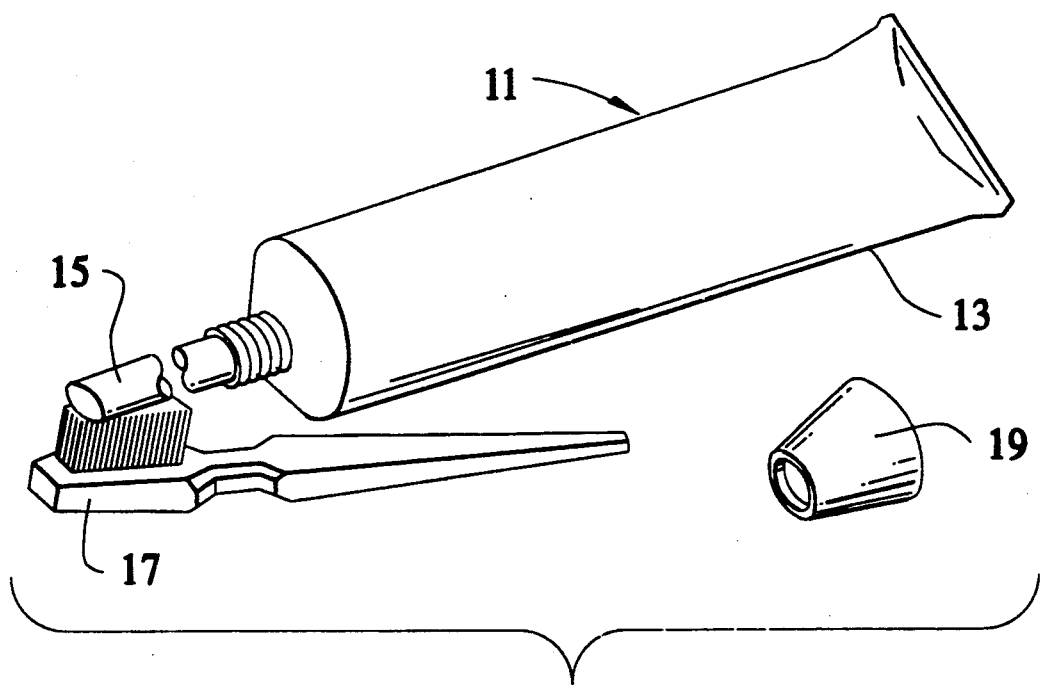
FIG. 1 is a perspective view of a toothpaste tube and its removed cap, with toothpaste having been squeezed from the tube onto a brush.

In FIG. 1 packaged anti-plaque toothpaste article 11 includes deformable toothpaste tube 13, which contains anti-plaque toothpaste 15, shown dispensed in a unitary amount such as about 0.8 to 2 grams by squeezing onto brush 17. Tube 13 is opaque and is made of a synthetic organic polymeric plastic material, such as polyfluoroethylene or is lined with such a material, as in a laminate, which does not adversely affect the anti-plaque activity of the toothpaste on storage. Alternatively, tube 13 may be made of or lined with a plastic which has been found to adversely affect anti-plaque action of the toothpaste (by decreasing the anti-plaque action of antibacterial and anti-plaque halogenated diphenyl ether component of the toothpaste) but in such case the ad-. verse effect on anti-plaque action is prevented or inhibited by the presence in the dentifrice of a stabilizing agent, which may be a terpene, e.g., limonene, or other effective flavor components. Preferably neither the toothpaste tube nor the cap 19 thereof nor any other part of the tube which may come into contact with the toothpaste (such as a liner for the cap) should be made of co-polyester/polyether elastomer or of other plastic which substantially diminishes the anti-plaque action of the oral preparation, even in the presence of a stabilizer for the anti-plaque component. It is also considered to be desirable to avoid the presence of other elastomers, such as isobutadienes, polychloroprenes, butadiene rubbers and nitrile rubbers, which might react with or absorb THDE. Desirably, such parts will be made of plastics which do not adversely affect anti-plaque activity, even in the absence of terpenes or other stabilizing agents in the dentifrice, but such other destabilizing plastics may be employed when such stabilizer is present in the toothpaste to counteract the inactivating effect of the plastic (except that elastomeric co-polyester/polyether and other adverse elastomers will preferably be avoided).

Figure 2:
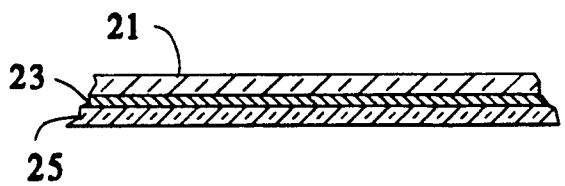
FIG. 2 is an enlarged partial sectional view of a laminated wall of a squeezable tube like that of FIG. 1.

In FIG. 2 there is shown a laminate of polyfluoroethylene film 21, aluminum sheet 23 and polyethylene film 25, with the polyfluoroethylene being on the inside of the tube wall, where it will be in contact with the toothpaste. The liner, not shown, for the cap 19 of FIG. 1, may also be of polyfluoroethylene, so that all surfaces in contact with the toothpaste during the storage are compatible with the halogenated diphenyl ether antibacterial component of the toothpaste and do not promote excessive losses of its anti-plaque activity on storage. Instead of having the inner wall 21 of the laminate of polyfluoroethylene, it may be of polyethylene and wall 21 may be of polyethylene or other suitable polymer.

Figure 3:
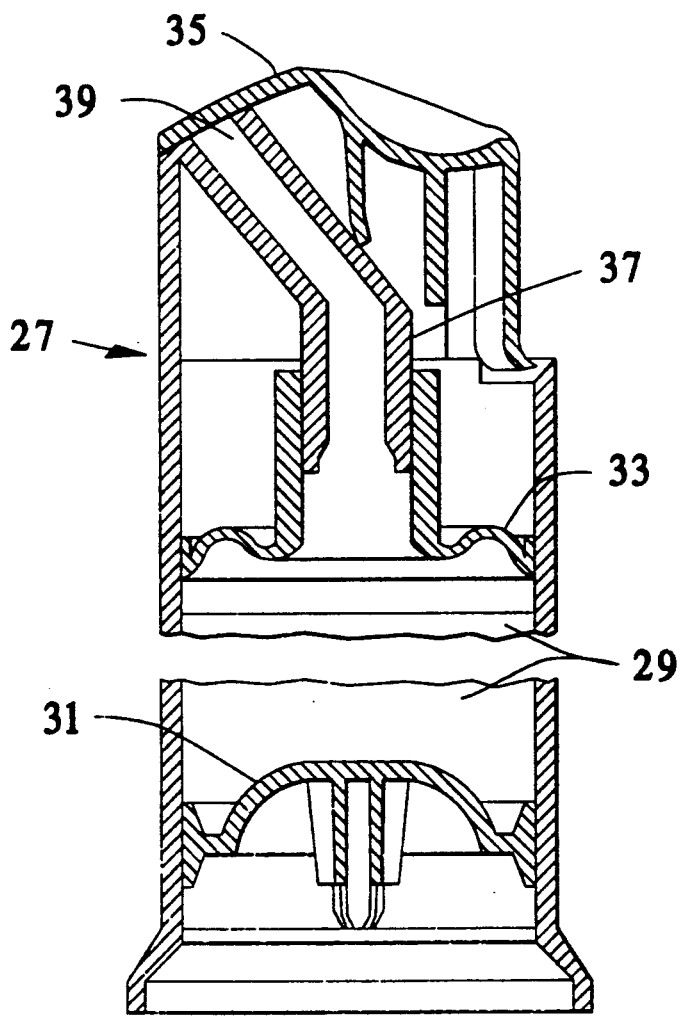
FIG. 3 is a vertical sectional elevation of a pump dispenser for containing and dispensing toothpaste or dentifrice gel, as desired.

In FIG. 3 the pump dispenser for toothpaste is of a type marketed by Guala S.p.A., of Italy, which is the subject of U.S. Pat. No. 4,776,496. Pump dispenser 27, when ready for use, contains toothpaste in compartment 29, which is defined by bottom wall 31 and membrane 33. Depression of actuating lever 35 causes a downward movement of membrane 33, forcing toothpaste through conduit 37 and out spout 39. When pressure on the actuating lever 35 is released membrane 33, which is elastic, returns to its original configuration and moves conduit 37 and lever 35 back to their initial positions. At the same time, bottom 31 is pushed upwardly by atmospheric pressure. The various internal parts of the pump dispenser that contact the toothpaste are preferably of plastic(s) that do not inactivate the halogenated diphenyl ether antibacterial and anti-plaque agent. However, in the event that it is not feasible to utilize plastics that have the necessary physical properties for the various contacting parts and still are compatible with the anti-plaque agent other plastics may be employed, providing that the toothpaste composition (or gel dentifrice) includes a stabilizing substance, such as limonene or other operative terpene or flavor component. However, it is considered best to avoid employing any co-polyester/polyether elastomers, especially for the pumping membrane (33), which plastic appears to be especially active against THDE in oral compositions of the types described.

Figure 4:
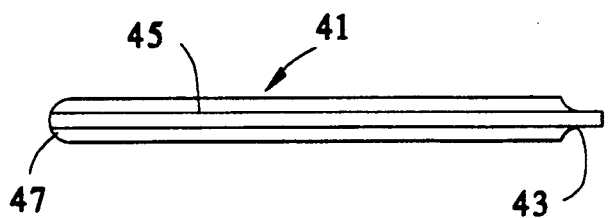
FIG. 4 is a side elevational view of a heat sealed sachet or pouch containing a single use amount of a toothpaste.

In FIG. 4 sachet, pouch or packet 41 is shown as a heat sealed unit, with heat sealing about three sides thereof, represented by numerals 43 and 45. The fourth side 47 is merely folded back on itself and need not be heat sealed. Inside the sealed packet is an oral composition, such as toothpaste, not shown, and the interior surface of such sachet is of a plastic material which does not promote excessive loss of anti-plaque action of the antibacterial compound of the contained oral composition. As with the other containers for the anti-plaque oral compositions, laminates may be utilized, with a plastic layer on the interior thereof which does not adversely affect the antibacterial agent, or when the plastic does have such a negative affect, it may be counteracted by the presence in the oral composition of a suitable stabilizer, which is preferably also useful as a flavoring agent thereof.

Figure 5:
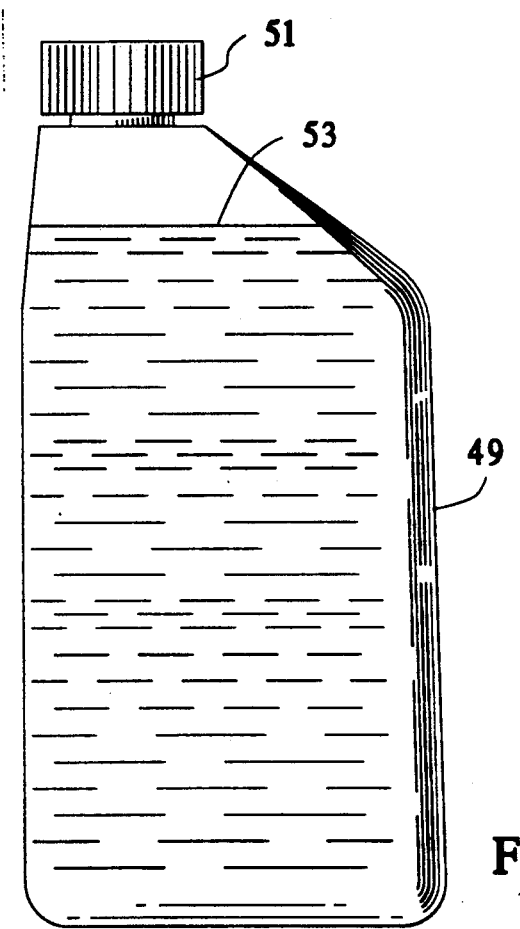
FIG. 5 is an elevational view of a capped bottle of mouthwash.

In FIG. 5 is shown an opaque bottle 49 having sealing cap 51 thereon. Both the bottle and the sealing insert (not shown) in the cap are of plastic materials which are compatible with the THDE that is the anti-plaque component in the mouthwash 53 contained in the bottle. As in the other examples given, when a "reactive" plastic is employed as the material of the inner portion of the bottle or of the cap seal a suitable stabilizer will be present in the mouthwash to prevent excessive loss of anti-plaque action of the THDE or other halogenated diphenyl ether.

In addition to the compositions described as being present in the illustrated packages, which include gel dentifrices and thick liquids instead of toothpastes, there may also be incorporated in such packages tooth treating compositions suitable for professional use, such as tooth hardeners, which may include fluorides and phosphates, compounded antibacterial agents, plaque-indicating dye solutions and other suitable oral compositions. Also, pressurized or "aerosol" compositions containing the mentioned anti-plaque compounds may be packed in pressurized containers (usually pressurized with gaseous nitrogen) providing that contacting plastic parts of such containers are of materials which do not cause excessive losses of anti-plaque properties of the anti-plaque agent in the contained toothpastes or other oral compositions.

In addition to the various containers illustrated in the drawing and mentioned above there may also be employed squeeze bottles, capsules, jars, sponge-like media and various types of mechanical dispensing containers. Because some of the halogenated diphenyl ether antibacterial compounds are photosensitive it will sometimes be desirable for such containers to be composed of, coated or laminated with a chemical or physical light screening material, many of which are known, to prevent transmission to the oral composition and to the anti-plaque compound of any inactivating radiation, e.g., ultraviolet light. Also, such containers will often desirably be opaque to prevent such actinic radiation from inactivating the anti-plaque component of the contained oral preparation, such as a toothpaste.

The cause(s) of inactivation by plastics of THDE and other substantially non-cationic antibacterial agents that have anti-plaque properties in oral compositions has/-have not yet been established. Research to date has not pinpointed the mechanism responsible for losses of such desirable activity but so far the results do not conclusively point to either chemical reactions or physical absorptions. Tests of basic mouthwash or mouth rinse formulations containing THDE show that when such a mouthwash or mouth rinse is aged in dispensing containers at room temperature, 38° C. and 49° C., for up to twelve weeks, there are "excessive" losses (over 25% of the initial concentration of THDE) when the mouth rinse has been in contact with such container walls and parts of low density polyethylenes, high density polyethylenes, polyethylene terephthalates, polypropylenes, nylons, polyallomers and polymethylpentenes. Similarly, high losses result when such storage is in containers with inner walls or parts of co-polyester/polyether elastomers, such as those which have previously been employed in Guala pump membranes. It was found that polyfluoroethylenes, such as polytetrafluoroethylenes, polyvinyl chlorides, polycarbonates and polysulfones did not absorb or react with excessive proportions of the THDE. However, polycarbonates and polysulfones are brittle and hence often are unsuitable for employment as dispensing container parts. Polyvinyl chlorides sometimes impart a foreign taste to oral compositions, such as toothpastes, and therefore will often be avoided as a container material, except in certain cases where such taste is compatible with the taste of the toothpaste flavoring employed. Thus, of all the polymeric plastic materials available, polyfluoroethylene is especially identified as a feasible material for use in the present containers or packages which does not seriously diminish the anti-plaque activity of the anti-plaque agents. However, as was indicated previously, by incorporating in the oral compositions stabilizing compounds for the anti-plaque agents, such as terpenes, of which limonene is representative, essential oils (which often contain terpenes), and other flavor components with similar "stabilizing" properties, one is able to reduce the activity losses of the antiplaque agents when they are in contact with containers or container parts made of the various mentioned polymeric plastics with which excessive losses in antiplaque activity occur. Therefore, one need not be dependent on polyfluoroethylene as a container dispenser material, providing that the oral composition also contains a stabilizing proportion of terpene or other suitable "stabilizer". When such stabilizer is present in the oral compositions or when polyfluoroethylene (or polyvinyl chloride, polycarbonate or polysulfone) is the only polymeric plastic in contact with the oral composition, storage losses of anti-plaque activity are less than 25%, and preferably will be less than 10%, even after ambiant to relatively high temperature storage, for example 20° to 40° C., for periods of time of several weeks to up to a year or more. It is considered that the most stable oral compositions are those which include a stabilizing proportion of terpene or other suitable stabilizer and also include contacting container parts only of polyfluoroethylene (or any of the other unreactive plastics). Although the terpenes and essential oils are the primary stabilizers according to the present invention, other flavor components may also contribute to the stabilization of the anti-plaque material, either by interfering with any destabilizing reaction or by inhibiting absorption of the halogenated diphenyl ether by the plastic (or by other unknown mechanism). Thus, it has been theorized that some components of the oral compositions that tend to solubilize the THDE can act to maintain it in the oral composition and inhibit or prevent its migration into the plastic. On the other hand, it has also been theorized that such a solubilizing action could promote migration of the solubilized THDE into the plastic. Because the issue has not been resolved applicants are not bound by either theory. Also, while it is desirable for the terpenes and other stabilizers to be flavor components, that is not necessary, and the stabilizers may be useful for only a stabilization purpose.

Although it is preferred that the packages of this invention include internal walls (in contact with the compositions) of or lined with solid synthetic organic polymeric plastic material, it is within the invention to utilize other solid (and/or film-forming) polymeric materials, whether or not they are synthetic, organic or even plastic. Thus, polyethylene glycols and methoxypolyethylene glycols, such as those of the Carbowax ® type, e.g., Carbowax 4,000 and Carbowax 6,000, may be employed, often as lining materials in dispensing containers of the described compositions. Inorganic silicon polymers, such as siloxanes, and non-synthetic organic film-forming materials, such as gums, e.g., carrageenan, tragacanth, karaya, are also useful as liners for dispensers. Additionally solid polymeric materials, such as cellulose and starch and derivatives thereof, are also useful as container materials in contact with the contained antibacterial and antiplaque components of the present packaged oral compositions.

The various oral packaged compositions of this invention that are most frequently made are toothpastes, dentifrice gels and mouthwashes (sometimes called mouth rinses). The former two will be referred to herein as dentifrices and the last will usually be called mouthwashes. Dentifrices comprise three major groups of component, the vehicle, polishing material and surfactant (or detergent). The antibacterial agent, e.g., halogenated diphenyl ether, is normally present in the vehicle, which vehicle usually comprises about 10 to 80% (all figures are on a final composition basis) of the dentifrice. Of the vehicle, about 3 to 40% will be water, about 7 to 77% will be humectant, such as glycerol, sorbitol, propylene glycol or mixtures thereof and 0.5 to 10% will be gelling agent, such as sodium carboxymethyl cellulose, Irish moss, iota carrageenan or hydroxyethyl cellulose or the like including mixtures thereof. The polishing material of the dentifrice will normally be from about 10 to 75% thereof in a gel or toothpaste or about 50 to 99% in a powder and such polishing material may be colloidal silica, precipitated silica, sodium aluminosilicate, insoluble sodium metaphosphate, hydrated alumina, calcined alumina, dicalcium phosphate dihydrate, anhydrous dicalcium phosphate or calcium carbonate, other known materials, or mixtures thereof. The surfactants include anionic, nonionic, cationic and zwitterionic surfactants but often the employment of nonionic surfactant is avoided because of its adverse affect on the antibacterial compounds, e.g., THDE, and the employment of cationic and zwitterionic surfactants are also often avoided because they tend to stain or darken the teeth. Thus, synthetic organic anionic surfactants, which are also detergents, are the preferred cleaning agents in the dentifrices, and of these, sodium lauryl sulfate and other sodium higher alkyl sulfates of 10 to 18 carbon atoms in the alkyl groups thereof are preferred, although various other well known sulfated and sulfonated detergents may be substituted for them, at least in part. Other active ingredients, such as fluoride-providing compounds, e.g., sodium fluoride or sodium monofluorophosphate, may be present to harden the teeth, usually in proportions providing about 0.001 to 1% of fluoride to the composition, and adjuvants, such as flavoring and sweetener, in proportions of 0.1 to 10%, may be utilized. Additionally, it may be desirable to employ a polycarboxylate, such as polyvinyl methyl ether maleic anhydride (PVM/MA) copolymer (Gantrez ®) in an amount corresponding to about 0.5 to 4% of the dentifrice. Such polycarboxylate material has been found substantially to improve the anti-plaque action of the antibacterial compound. Use of such polycarboxylates in oral compositions is described in U.S. Pat. No. 4,627,977, which description is incorporated herein by reference.

In mouthwashes the oral vehicle is preferably aqueous and alcoholic, with the alcohol being ethanol or isopropanol. The vehicle will normally be 90 to 99.9% of the composition, of which the alcohol is 5 to 30% and propylene glycol is often 2 to 10%, on a final product basis. The remainder of the composition, 0.1 to 10%, may include flavor, surfactant, sweetener, colorant, anti-plaque agent and other adjuvants for specific purposes. In dentifrice and mouthwash compositions the effective amount of antibacterial anti-plaque compound(s) will normally be in the range of 0.02 to 0.2%, more preferably 0.03 to 0.1% in mouthwashes, and normally about 0.25 to 1%, more preferably 0.25 to 0.5 or 0.6% in dentifrices, with the proportion ranges not exceeding 0.8% for THDE in toothpastes and not exceeding 0.2% THDE in mouthwashes (because of possible mouth numbing effects at higher concentrations), and not being less than indicated in order to avoid ineffectiveness against plaque at low concentrations. Preferably the dispensed compositions will contain proportions of the anti-plaque agent and THDE within the given ranges but when the initial concentration thereof is within the given range a loss of up to 25% may be acceptable and such dispensed compositions are within the scope of the invention.

To stabilize oral compositions that are to be packaged in containers containing plastic walls or other parts, wherein the plastics are those which are "reactive" with the antibacterial compounds, 0.01 to 2% of terpene(s) or stabilizer(s) will desirably be present in the oral compositions, preferably 0.05 to 1% and more preferably 0.1 to 0.5%. Such stabilizers may be present in a suitable flavoring agent for the dentifrice, if desired (and it often is), and will be at least 5% of the flavor, preferably at least 10%, more preferably at least 25% and most preferably at least 50%.

Although the above description is primarily relevant to dentifrices and mouthwashes, other oral compositions (e.g., including chewing gums) of the invention will contain similar proportions of components, depending on the form of the composition (liquids containing less, as in the mouth rinses, and thicker compositions containing more as in the toothpastes), often with the additions of specific agents for accomplishing the purposes of such compositions. Thus, tooth hardening compositions may include fluorides and phosphates, such as sodium or potassium fluoride and sodium fluorophosphate, in either dentifrice or mouthwash bases, often in percentages in the range of 1 to 5%. Plaque-indicating dye solutions may include a suitable dye (red is apparently the most favored color for such products), often at a concentration in the range of 0.001 to 0.1%, in a mouthwash base. The compositions of the other products will be adjusted accordingly, as will be known to those of skill in the art.

The antibacterial agent is a non-cationic material which is water insoluble or essentially water insoluble (having a solubility in water at 25° C. of less than 10 g./l., and sometimes less than 1 or 0.1 g./l.) Such materials are soluble or dispersible in dentifrice vehicles that contain glycerol, sorbitor and/or propylene glycol, and in final products based on such media. They are also soluble or dispersible in the aqueous alcoholic media of mouthwashes.

Of the antibacterial agents, the halogenated diphenyl ethers will normally contain bromine and/or chlorine, with chlorine being the preferred halogen. They will preferably be substituted with 1 to 3 hydroxyls and 1 to 4 halogens. More preferably they will be substituted with 1 or 2 hydroxyls and 2 or 3 halogens, preferably with four substituents, two on each ring. Among the more preferred of such compounds are 2, 2'-dihydroxy- 5,5'-dibromo-diphenyl ether and 2', 4, 4'-trichloro-2-hydroxy-diphenyl ether, with the latter compound (THDE) being most preferred. Various replacement halogenated phenolic, non-cationic, substantially water insoluble antibacterial anti-plaque compounds, such as those itemized at pages 2-8 of application Ser. No. 07/398,566, U.S. Pat. No. 5,032,386 filed Aug. 25, 1989, which application is incorporated herein by reference, will be substituted in whole or in part for the halogenated diphenol ethers, when that is considered to be appropriate.

The terpenes, which term, for the purpose of this specification, includes the terpene hydrocarbons and oxygenated derivatives thereof, include such compounds as dl-limonene, menthol, diterpenes, polyterpenes and derivatives thereof, many of which are found in various essential oils and other flavors. In addition to being useful as stabilizers for halogenated diphenyl ethers they often contribute desirable flavors to the present oral compositions. Of the terpenes and their derivatives it is considered that limonene best balances these properties, although other terpenes, including those which are not flavors, are also useful, as are other emulsifiable lipophilic essential oils and flavoring agents which contain stabilizing components.

The various plastics that were previously described as the components of container and/or dispenser parts have been described only briefly because it is considered that their chemical natures and degrees of polymerization are well known, so detailing thereof is unnecessary in this specification. If further details are wanted reference should be made to *Modern Plastics Encyclopedia*, which is published on an annual basis by McGraw-Hill Inc., New York, N.Y.

As was described in incorporated Ser. No. 07/398,566, U.S. Pat. No. 5,032,386 the compositions (of the invention) may contain a source of fluoride ions, capable of supplying 25 to 5,000 ppm of fluoride ion in the oral cavity, preferably 300 to 2,000 ppm and more preferably 800 to 1,500 ppm. See incorporated U.S. Pat. No. 4,627,977 for further details about suitable fluorides, proportions and manufacturing details. The fluoride acts primarily as a tooth hardener but also serves to stabilize polyphosphate anti-calculus compound when present. Such polyphosphate is preferably a mixture of sodium and potassium pyrophosphates and it is also stabilized by Gantrez S-97. Proportion ranges are given in U.S. Ser. No. 07/398,605, abandoned, filed Aug. 25, 1989, which application is incorporated herein by reference, and in incorporated U.S. Pat. No. 4,627,977 and U.S. Pat. No. 4,806,340, which is incorporated herein by reference.

For other details of formulations, components, adjuvants, manufacturings and uses, see the patent, specifications and applications previously mentioned in this specification, which are hereby incorporated by reference.

Manufacture of the described oral compositions is by any of various standard techniques for producing such classes of compositions. Referring to specific examples for simplicity, the THDE is dispersed and/or dissolved in the vehicle portion of the dentifrice and the terpene is present in the flavoring agent. To make a dentifrice, the vehicle is prepared containing glycerol, sorbitol, and propylene glycol, gelling agents and suitable adjuvants (including Gantrez ® S-97 and triclosan), and the vehicle and aqueous anionic detergent (preferably sodium lauryl sulfate or a mixture of sodium lauryl sulfate and sodium methyl cocoyl taurate) solution are mixed, followed by blending in of the polishing agent component with the pre-mix. Finally, flavoring agent, including terpene, dissolved in ethanol, is admixed and the pH is adjusted. To make the mouthwash the various components thereof are merely admixed into the alcohol or aqueous alcoholic medium and are stirred until dissolved. A mix of sodium lauryl sulfate (SLS) and sodium methyl cocoyl taurate (of a ratio in the range of 1:4 to 4:1) is preferably employed as the anionic surfactant component of the mouthwash, with the presence of the taurate permitting a correspondingly desirable decrease in the SLS content, which is desirable. Other oral compositions are prepared according to similar relevant procedures.

In packaging of the oral composition into the dispensing containers, it will be desirable to avoid contacting of the compositions with plastic parts of co-polyester/polyether elastomer and it will also be desirable to avoid contacting of any compositions not containing stabilizing agent (such as terpene or flavor containing it) with plastic parts made of those plastics previously listed in this specification as reactive with THDE and other such antibacterial and anti-plaque compounds. It will be especially important to avoid the mentioned plastic parts for holding tanks or any other containers, piping, pumps or equipment in which the oral composition may be held for any appreciable length of time or held for shorter lengths of time at elevated temperatures.

Even when the packaged compositions of this invention are prepared and contacts of the oral compositions containing THDE or other halogenated diphenyl ether antibacterial composition with the reactant plastics are avoided it will still be desirable to minimize exposures of such packaged compositions to heat and to light, both of which have been found to accelerate loss of anti-plaque activity. Thus, the invented compositions are preferably stored and packaged in opaque containers and dispensers at a temperature in the range of 10° to 38° C. and are stored at such a temperature, too. Otherwise, the packaged compositions may be stored and used in normal manner and the desirable anti-plaque effects thereof will be obtained. Such effects have been verified by laboratory testing and by evaluations of the teeth of volunteers serving on human panels, who employed the various packaged compositions and controls as directed. Significant improvements in anti-plaque activities of the packaged compositions of this invention are observed, compared to control packaged compositions wherein the packaging included plastic parts that were "reactive" with the halogenated diphenyl ether antibacterial compound and which do not contain stabilizing agent in the oral composition. Such improvements are also found when packages made of "reactive" plastics (but not co-polyester/polyether elastomers) are employed with oral compositions containing terpenes and are compared to controls in which the oral compositions contains no terpenes and no flavoring agents.

The following examples illustrate but do not limit the invention. Unless otherwise indicated, all percentages and proportions in these examples, the specification and the appended claims are by weight, and all temperatures are in °C.

EXAMPLE 1

| Component | Percentage |
| --- | --- |
| Water, deionized | 47.84 |
| Sorbitol (70% aqueous solution) | 20.00 |
| Ethanol (95% aqueous solution) | 12.50 |
| Glycerol | 10.00 |
| Propylene glycol | 7.00 |
| *Gantrez S-97 (13% solution) | 1.92 |
| Sodium hydroxide (50% aqueous solution) | 0.12 |
| Sodium lauryl sulfate | 0.25 |
| **Tauranol WSHP | 0.20 |
| ***Flavor Mixture | 0.12 |
| ****Triclosan (Irgasan ® DP 300, manufactured by CIBA-GEIGY) | 0.05 |
| | 100.0 |

*Polyvinyl methyl ether/maleic anhydride copolymer (GAF Corp.)
**Sodium methyl cocoyl taurate
***Contains at least 25% terpenes, including at least 25% of limonene
****THDE (2',4,4'-trichloro-2-hydroxy-diphenyl ether)

The mouth rinse (or mouthwash) of this example is made by mixing together the various listed components in any suitable order, according to standard procedures, but preferably the triclosan is first dissolved in the propylene glycol and ethanol mixture, after which it is mixed with an aqueous solution of sorbitol, glycerol and the anionic surfactants, with the flavor mixture being added last. The sodium hydroxide solution is employed for neutralization of the resulting acidic mixture, which neutralization is to a pH of 6.84 (it being desirable to have the product at or near to a neutral pH).

The mouth rinse resulting is of excellent cosmetic stability and is of acceptable flavor, and the flavor and triclosan are satisfactorily dissolved, with such dissolving being at least partially attributable to the presence of the Tauranol WSHP. When only 0.25% of SLS is employed as the anionic surfactant solubilizations of the flavoring agent and triclosan are not as satisfactory. Although such solubilizations can be increased by using more SLS the maximum acceptable limit of such compound in the mouth rinses is often about 0.25%, and the Tauranol ® WSHP and SLS are safe and acceptable in the proportions employed. The described mouth rinse is tested in vitro for bioavailability of triclosan against comparable mouth rinses of formulas omitting the Tauranol WSHP, in one case, and replacing it with half as much of a nonionic surfactant (Pluronic F-127) in another case. By triclosan uptake tests, measuring triclosan absorption by hydroxyapatite discs that had been coated with saliva, and by protein absorption "zone of inhibition" tests it is found that the presence of the mixed anionic surfactant results in comparable bioavailability of triclosan, compared to such availability from the SLS-only formula, and such availability is significantly higher for the formulas containing no nonionic detergent than for that wherein the nonionic detergent (Pluronic ® F-127) is present.

The mouth rinse of the formula of this example is aged at elevated temperature (41° C.) for three and five weeks, which is considered equivalent to at least about six months and one year's actual aging at room temperature. Such aging tests are conducted in dispensing containers (bottles) made of glass, polyvinyl chloride and polyethylene terephthalate (or lined with the plastic materials). Although chemical analyses of the mouth rinses after such aging periods find no losses of triclosan when the container is glass, losses of triclosan from the mouth rinses are noted when the containers are of polyethylene terephthalate or of this sample of polyvinyl chloride but they are significantly less than a tolerable 25% (of the original concentration), and can be under 5 or 10%.

When, in place of the flavor mixture, dl limonene is employed in 0.1, 0.2 and 0.4% quantities, even better stabilizations of the triclosan in the described package dentifrices of the invention are obtainable, and such stabilizations also result when other terpenes from any of various essential oils, and flavoring agents, are present in similar proportions. Such good results are also obtainable when the container material or the liner thereof is of polymethyl pentene, polyallomer, polypropylene, high and low density polyethylenes, and nylon, although such materials, in the absence of the flavor mixture (and contained terpenes) cause significant and excessive losses of available triclosan from the mouth rinse on storage, especially at elevated temperatures.

EXAMPLE 2

| Component | Percent |
| --- | --- |
| Water, deionized | 84.42 |
| Ethanol (95%) | 10.0 |
| Propylene glycol | 5.0 |
| Sodium lauryl sulfate | 0.50 |
| Triclosan | 0.06 |
| Sodium saccharin | 0.02 |
| | 100.00 |

A mouth rinse of the above formula is tested for triclosan availability after storage for three weeks in dispensing containers made from or lined with various plastics. Testings are at room temperature, 38° C. and 49° C., with the elevated temperature storages simulating lengthier storage times, up to a year or more at room temperature. Losses of over 25% of the triclosan from the stored mouth rinse are noted when the containers are polymethyl pentene, polyallomer, polypropylene, high and low density polyethylenes and nylon, with unacceptable results (excessive losses) being noted when the containers are polypropylene, polyethylene and nylon (with nylon being the worst).

When the container material or liner is polyvinyl chloride, polycarbonate, polysulfone or polyfluoroethylene, e.g., polytetrafluoroethylene or Teflon ®, essentially no losses of triclosan occur. Losses of triclosan from mouth rinses stored in containers of or lined with the polymers mentioned (polymethyl pentene, etc.) may be decreased in the same manner as described in Example 1 by incorporating in the mouth rinse formula limonene, other terpenes, or essential oils in which such may be present, with the proportion of terpene preferably being at least 0.1%, and more preferably being greater, e.g., 0.2% or 0.4%, on a final composition basis. In some instances even the employment of flavoring material which does not contain any significant proportion of terpenes will have a positive effect, although such effect will not be expected to be as good as with terpenes in the formulation.

EXAMPLE 3

| Component | Percent |
| --- | --- |
| Propylene glycol | 10.00 |
| Iota carrageenan | 0.75 |
| Sodium fluoride | 0.33 |
| Sorbitol (70%) | 30.00 |
| Sodium saccharin | 0.30 |

| Component | Percent |
| --- | --- |
| Titanium dioxide | 0.50 |
| Sodium hydroxide (50% aqueous solution) | 0.80 |
| Water, deionized | 27.71 |
| +Luviform TM (35% solution) | 4.76 |
| ++Zeodent TM 113 | 20.00 |
| +++Sident TM 22S | 2.00 |
| Sodium lauryl sulfate (94% active) | 1.60 |
| Flavor | 0.95 |
| Triclosan | 0.30 |
| | 100.00 |

+Polyvinyl methyl ether/maleic anhydride copolymer (BASF Corp.)
++Silica polishing agent (J. M. Huber Corp.)
+++Silica thickening agent (Degussa Co.)

A dentifrice of the above formulation is made in normal manner and is employed as a medium for testing the stability of triclosan when the dentifrice containing it is exposed to different plastics which are employed as materials of containers or of parts of the dispensers in which dentifrices are stored and from which they are dispensed. The plastics for the tests are Pibiflex TM 46, made by Inmont, and Arnitel TM 460 EM, mf'd. by AKZO, which are plastics that are employed as the membranes or bellows of a pump dispenser, as illustrated in FIG. 3. Six samples of plastics are tested, three of each of the three mentioned plastics, with each of the three being treated with a different mold release agent (to determine whether the nature of the release agent is relevant to the problem of triclosan stability in contact with plastics during storage). The release agents are Silicon Master TM (5% silicone oil and 95% polypropylene), Silicone Master plus Silicone Oil (with extra silicone oil) and Armid O Master TM (5% oleo amide and 95% polypropylene), respectively. After two weeks storage of the test samples in contact with the dentifrice at different temperatures (room temperature, 38° C. and 49° C.), the dentifrice is removed from the plastic container materials and the plastics are washed with water and immersed in methanol to dissolve any triclosan which might have been taken up by them during storage. The methanol washings are collected and are analyzed, using high performance liquid chromatography. It is found that essentially the same types of absorptions of triclosan take place with the different membrane materials and although there are variations between them and such are somewhat dependent on the release agents employed, the results are essentially the same in all cases. The co-polyester/polyether elastomers are found to absorb significant percentages of triclosan from the dentifrice, which results are confirmable when the co-polyester/polyether elastomers are used as bellows materials in pump dispensers containing the described dentifrice and other dentifrices within the invention. Accordingly, it is considered undesirable to employ co-polyester/polyether elastomers in contact with the present dentifrices or mouthwashes, even when the dentifrices and mouthwashes contain flavoring materials which include terpenes (which are present in the flavoring of the dentifrice formulation), to the extent of at least 0.1% of the dentifrice.

When the tests are repeated, using actual Guala pump dispensers as containers for the dentifrices, with co-polyester/polyether elastomer membranes of Arnitel TM, the losses of triclosan are also unacceptable but when the co-polyester/polyether elastomer is replaced by others of the acceptable plastics, e.g., polyfluoroethylene, the triclosan activity is improved to within acceptable limits. Also, other plastic parts of such pump dispensers, such as polypropylene inner walls thereof, are not found to absorb excessive amounts of triclosan and do not seriously decrease the anti-plaque activity of the dentifrice, apparently due to the presence of terpenes in the flavoring agent of the contained dentifrice.

A panel test is run, involving at least ten human subjects, who employ the dentifrice of this example, dispensed from polyethylene terephthalate and polyethylene lined tubes, in twice-a-day brushings for one month, during which time plaque evaluations of the subjects' teeth are made by trained observers. The test results establish that the dentifrice composition has a definite anti-plaque activity, similar to that which is also observable in tests with the mouth rinses of Examples 1 and 2, and also prove that the triclosan has not been unacceptably inactivated, and still is present in an effective anti-bacterial and anti-plaque proportion in the dentifrice.

EXAMPLE 4

| Component | Percent |
| --- | --- |
| Glycerol | 7.00 |
| Propylene glycol | 3.00 |
| Iota carrageenan | 0.75 |
| Sorbitol (70%) | 30.00 |
| Sodium saccharin | 0.30 |
| Sodium fluoride | 0.33 |
| Titanium dioxide | 0.50 |
| Gantrez ® S-97 (13% solution) | 15.00 |
| Deionized water | 16.07 |
| Sodium hydroxide (50% aqueous solution) | 0.80 |
| Zeodent ® 113 (J. M. Huber Corp.) | 20.00 |
| Sylodent ® 15 (a silica thickener; W. R. Grace Corp.) | 3.00 |
| Flavoring agent | 0.95 |
| Sodium lauryl sulfate | 2.00 |
| Triclosan | 0.30 |
| | 100.00 |

A toothpaste of the above formula is made and is stored in Guala TM pump dispensers having bellows membranes of the Arnitel type. The dentifrice is also filled into laminated tubes, having polyethylene terephthalate on the interior of the laminate, in contact with the dentifrice. The dentifrices are aged at 5° C., 25° C., and 39° C., for two, four and six weeks. After such aging periods, the dentifrices are dispensed at the rate of about 1.5 grams per day and at weekly intervals the triclosan contents of the dispensed dentifrices are determined by analyses. In the case of the Guala pump dispenser the dispensed dentifrice loses about 27% of the triclosan, which is excessive and objectionable. The loss is about constant, regardless of storage temperature or time of storage, which can be explained by absorption of the triclosan by the pump membrane, with which it is brought into contact prior to dispensing. Such membrane is of a co-polyester/polyether elastomer, which class of plastics is to be avoided as a container material or as a part in a container or dispenser for dentifrices containing triclosan. However, when the elastomeric co-polyester/polyether membrane is replaced by one made of any of the previously mentioned acceptable plastics, such as polyethylene terephthalate, which can serve as membrane materials in modified pump dispensers (modified to compensate for different properties of such plastics), triclosan stability is increased and the dispensed composition is satisfactory and effective as an anti-plaque toothpaste.

Gel toothpaste formulations in such packages behave similarly with respect to triclosan stability after storage and on dispensing.

In similar tests, using polyethylene terephthalate lined tubes little loss (less than 5%) of triclosan is noted, indicating that the presence of the terpenes (0.1% or more of the composition), including limonene, in the flavoring agent (or the flavoring agent itself) prevents loss of the triclosan or inactivation thereof. When polyfluoroethylene-lined tubes are employed there will be little loss of triclosan even when the flavoring agent is omitted from the dentifrice composition and such will also be the case when polyvinyl chloride is employed as the liner material in contact with the dentifrice or when polysulfone or polycarbonate package parts are in contact with such dentifrice. However, as was indicated previously, one will not usually employ such three last named plastics.

When in the reported test in which the dentifrice is dispensed from the Guala dispenser the Gantrez S-97 is replaced by 4.76 parts of Luviform (35%), with the difference being made up in deionized water, no appreciable difference in triclosan stability is noted between the formulas.

In the above formulas the polishing system is a siliceous system rather than one based on alumina. When the polishing agent is changed to an alumina, the problems previously mentioned as having been noted with some plastics are decreased but still exist. Also, the presences of terpenes in the dentifrices promote triclosan stability, as such presences do in similar dentifrice compositions based on siliceous polishing agents.

EXAMPLE 5

The mouth rinses and the dentifrices of the foregoing examples may be varied in composition ±10% and ±25% for the various components thereof, providing that such percentages are not outside ranges given elsewhere in this specification, and operative and effective antibacterial and anti-plaque products are obtainable, which are dispensable in effective anti-plaque state from the mentioned dispensing containers that are made of compatible plastics. The products may also be modified by being converted to dentifrice gels, oral gels, pastes, liquids, lozenges, capsules, tablets, and sachets of the types previously mentioned in the specification. Such products also will behave in similar manners, with the triclosan or other halogenated diphenyl ether or antibacterial anti-plaque agent being sufficiently stable in the presence of polyfluorethylene, polyvinyl chloride, polycarbonate and polysulfone packaging or package component materials, even when no flavoring agent and no terpenes are present in the oral compositions, and being stable in the presence of polyethylenes, polypropylenes, polyethylene terephthalates, polyallomers, nylons and polymethylpentenes, as package or component materials, providing that a terpene, such as limonene, or a stabilizing flavor component is present in the oral composition. As with the other dentifrices and mouthwashes previously discussed, because of excessive absorption or other adverse action with respect to triclosan by co-polyester/polyether and other elastomers, uses of such materials will preferably be avoided.

EXAMPLE 6

Dentifrices of the formulas of Examples 3 and 4 are made and are dispensed after one month's storage at 30° C. in collapsible toothpaste tubes lined with polyethylene, in one case, and polyethylene terephthalate, in another, onto bristled toothbrushes, as illustrated in FIG. 1. The amounts of toothpaste on the toothbrush are in the range of 0.8 to 2.0 grams with 1 to 1.5 g. being preferred. When 1.5 g. is dispensed the active triclosan in the dentifrice on the brush is about four milligrams (with only 10% of the triclosan being inactivated). When storage is for a longer time or at higher temperature or with a more destabilizing plastic in contact with the dentifrice during storage the packaged compositions can contain about 3 mg. of triclosan in the 1.5 g on the brush. Thus, with 1 g. of dentifrice on the brush the amounts of triclosan will be about 2.7 mg. and 2 mg. respectively. For dentifrices containing from 0.25 to 0.6% of triclosan the toothbrush can contain from 2.2 to 8 mg. of triclosan if the triclosan inactivation is in the 10 to 25% range, or up to about 9 mg. when no triclosan is inactivated.

The described packaged dentifrices are employed to brush the teeth with typically about 0.8 to 2 g being dispensed onto toothbrushes for each brushing. Brushings are twice a day, morning and night, one minute at a time, for four weeks, after which definite improvement in anti-plaque action is apparent, compared to a control dentifrice that contains no triclosan. Improvement in anti-plaque action is also visible, compared to an unflavored control (containing no terpene) that contains triclosan in a dentifrice package in polyethylene and polyethylene terephthalate lined tubes.

The present invention has been described with respect to illustrative examples and embodiments thereof but is not to be limited to those because it is evident that one of skill in the art, with the present specification before him or her, will be able to utilize substitutes and equivalents without departing from the invention.

What is claimed is:

1. An article comprising a dispensing container having solid polyethylene or polyethylene terephthalate polymeric material in contact with an oral composition in the container, which composition comprises an effective antibacterial antiplaque proportion of a substantially water insoluble noncationic halogenated diphenylether antibacterial antiplaque agent and a stabilizer to make said polymeric material compatible with said agent in the presence of the oral composition, which compatibility is such that after three weeks storage at elevated temperatures less than about 25% of said agent is lost.

2. An article according to claim 1 comprising an opaque dispensing container.

3. An article according to claim 1 in which the composition is a toothpaste, gel or liquid dentifrice, a liquid mouthwash, or a paste, gel or liquid tooth treating agent and in which the container is a deformable dispensing tube, a pump dispenser, a pressurized dispenser, or a sachet for toothpaste, gel dentifrice, or paste or gel tooth treating agent, or a bottle or other container for a liquid dentifrice, mouthwash or tooth treating agent.

4. An article according to claim 1 in which the composition comprises a tooth hardening proportion of fluoride ions and an anti-tartar proportion of a polyphosphate or a mixture of polyphosphates.

5. An article according to claim 3 in which the composition is a toothpaste, gel dentifrice or liquid mouthwash, and wherein the halogenated diphenyl ether antibacterial agent comprises a diphenyl ether substituted with 1 to 3 hydroxyls and 1 to 4 halogens selected from the group consisting of chlorine and bromine, and in which the container is a deformable dispensing tube, a pump dispenser or a sachet for the toothpaste or gel dentifrice, or is a bottle or other dispensing container for the liquid mouthwash.

6. An article according to claim 1 wherein the halogenated diphenyl ether antibacterial agent comprises 2′,4,4′-trichloro-2-hydroxy-diphenyl ether (THDE) or 2,2′-dihydroxy-5,5′-dibromodiphenyl ether (DDDE).

7. A toothbrush containing on bristles thereof a toothbrushing quantity in the range of 0.8 to 2 grams, of a toothpaste or gel dentifrice of the composition defined in claim 6 that had been dispensed from the container of said claim 1 which quantity of toothpaste or gel dentifrice contains an effective anti-plaque amount of THDE.

8. An article according to claim 6 in which the composition comprises 0.02 to 1% of THDE and/or DDDE.

9. An article according to claim 6 in which the composition comprises 0.02 to 1% of THDE.

10. An article according to claim 6 in which the composition is a liquid mouthwash containing 0.03 to 0.1% of THDE and wherein the solid polymeric material in contact with the oral composition in the container comprises polyethylene.

11. An article according to claim 6 in which the composition is a toothpaste or gel dentifrice containing 0.25 to 0.5% of THDE in a deformable dispensing tube, a pump dispenser or a sachet and the solid polymeric material in contact with the oral composition in the container comprises polyethylene.

12. An article according to claim 6 in which the composition is a toothpaste or gel dentifrice containing about 0.3% of THDE and in which the container is a deformable dispensing tube or a pump dispenser.

13. An article according to claim 1 wherein the solid polymeric material which contacts the oral composition, comprises polyethylene.

14. An article according to claim 1 wherein the solid polymeric material in contact with the oral composition comprises polyethyleneterephthalate.

15. An article according to claim 1 in which the composition contains a stabilizing proportion of a terpene or flavoring agent as the stabilizer which stabilizes the antibacterial agent in the presence of said solid polymeric material.

16. An article according to claim 10 wherein the liquid mouthwash contains a stabilizing 0.01–2% proportion of a terpene or a flavoring agent as the stabilizer which stabilizes the THDE in the presence of said polymeric material in contact with the mouthwash.

17. An article according to claim 11 wherein the toothpaste or gel dentifrice contains a stabilizing 0.1–2% of a terpene or a flavoring agent as the stabilizer which stabilizes the THDE in the presence of said polymeric material in contact with the toothpaste or gel dentifrice.

18. An article according to claim 15 wherein the said polymeric material comprises polyethylene.

19. An article according to claim 15 wherein the said polymeric material comprises polyethylene terephthalate.

20. An article according to claim 15 wherein the terpene content of the stabilizer is in the range of 0.01 to 2% of the composition.

21. An article according to claim 20 wherein the terpene content of the composition is in the range of 0.1 to 0.5%.

22. An article according to claim 15 wherein the terpene is limonene.

23. An article according to claim 1 in which the composition comprises 0.5 to 4% of polyvinyl methyl ether maleic anhydride copolymer.

24. An article according to claim 4 in which the composition comprises fluoride ions and 0.5 to 4% of polyvinyl methyl ether maleic anhydride copolymer which, together, stabilize the polyphosphate(s) against enzymatic loss of anti-tartar action.

* * * * *